United States Patent [19]

Sweat

[11] Patent Number: 4,461,286

[45] Date of Patent: Jul. 24, 1984

[54] CHIROPRACTIC INSTRUMENT

[76] Inventor: Roy W. Sweat, 4735 River Ct., Duluth, Ga. 30328

[21] Appl. No.: 357,979

[22] Filed: Mar. 15, 1982

[51] Int. Cl.³ .................................................. A61F 5/00

[52] U.S. Cl. .................................................. 128/69

[58] Field of Search .................... 128/69, 54, 68, 24 R

[56] References Cited

U.S. PATENT DOCUMENTS

| | | | |
|---|---|---|---|
| 2,048,220 | 7/1936 | Redding | 128/69 |
| 2,078,159 | 4/1937 | Redding | 128/69 |
| 2,970,592 | 2/1961 | David | 128/69 |
| 3,706,309 | 12/1972 | Toftness | 128/69 |
| 3,949,731 | 4/1976 | Cass | 124/27 |
| 4,116,235 | 9/1978 | Fuhr et al. | 128/69 |

*Primary Examiner*—Stephen C. Pellegrino

*Attorney, Agent, or Firm*—Rodgers & Rodgers

[57] ABSTRACT

A chiropractic instrument comprises an elongated hollow tubular housing, an elongated thrust pin mounted within said housing and having one end projecting outwardly through one end of said housing, a percussion device reciprocably mounted within said housing and arranged with one part thereof normally spaced from the inner end of said thrust pin, releasable latch means arranged so as normally to secure said percussion device against reciprocable movement within said housing, and energy storage means arranged to impart bodily movement to said percussion device toward and into impingement with the inner end of said thrust pin in coordination with release of said latch means so as to establish an impulse wave along the length of said thrust pin without imparting significant bodily movement thereto.

9 Claims, 3 Drawing Figures

CHIROPRACTIC INSTRUMENT

TECHNICAL FIELD

This invention is for use in conjunction with chiropractic manipulation procedures and more particularly is for the purpose of adjusting or realigning the first cervical vertebra called the atlas and is of the type which is primarily adapted for use as a manually operable and bodily movable device although in its broader aspects the invention is not limited to such a mechanism.

BACKGROUND ART

Known chiropractic adjusting instruments utilize a thrust pin for engaging a patient's atlas and which is adapted for straight line forward bodily movement, such movement being effected to adjust or realign the patient's atlas.

Such prior art devices may sometimes cause injury to the patient being treated because the degree and force of movement of the thrust pin may cause injury.

DISCLOSURE OF THE INVENTION

According to this invention in one form, a thrust pin or stylus is mounted within a housing structure and is arranged with one end projecting outwardly through one end of the housing and a percussion device reciprocably mounted within the housing is normally latched in position relative to the housing but is driven by energy storage means into impingement with the inner end of the thrust pin in coordination with the release of the latch means so as to establish an impulse wave along the length of the thrust pin without imparting significant bodily movement to the thrust pin and by this means to effect appropriate realignment or adjustment of the atlas or of another vertebra against which the outer end of the thrust pin is in contact.

The impulse wave imparted to the thrust pin by the plunger excites a compressional wave in the thrust pin. The velocity of this wave in the thrust pin material is determined by the square root of the ratio of the Young's modulus to the density of the thrust pin material. At the patient thrust pin interface, dependent on the impedance match, a portion of this wave energy is transmitted into the patient and a portion is reflected back to the plunger.

BEST MODE OF CARRYING OUT THE INVENTION

Figures 1, 2, 3:
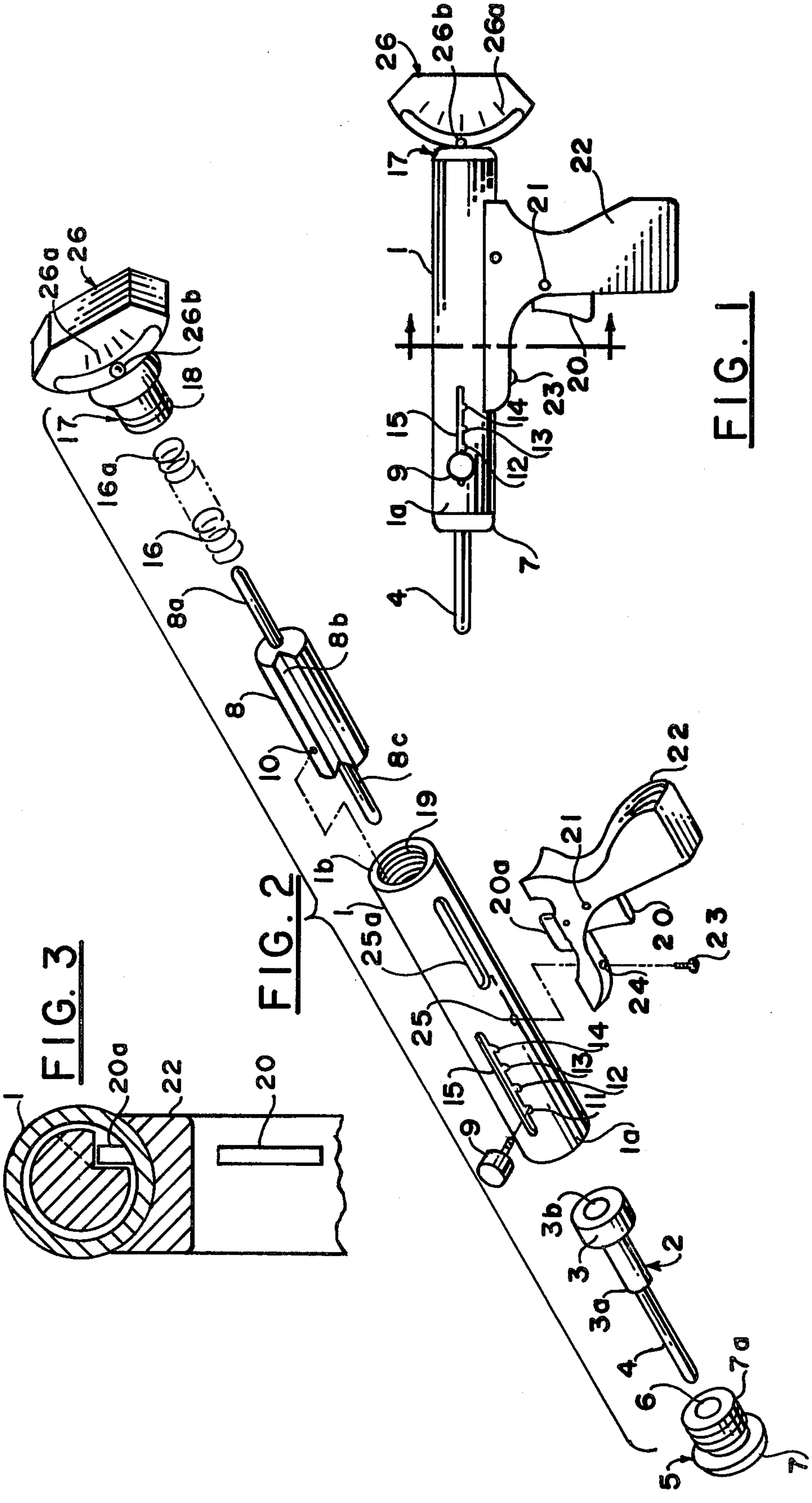
FIG. 1 is a side view of an instrument constructed according to this invention.
FIG. 2 is an exploded view of the structure shown in FIG. 1.
FIG. 3 is a cross sectional view taken along the line designated 3–3 in FIG. 1.

In the drawings the numeral 1 designates a hollow tubular elongated housing structure and the numeral 2 generally designates a thrust pin having a base portion 3,3*a* and an outwardly projecting stylus portion 4 which is of smaller diameter than the two step base portion 3,3*a*. An end cap 5 is provided with a central opening 6 and a flanged outer portion 7. The tubular threaded portion 8 is arranged for threaded mounting within the end 1*a* housing 1. The portion 3*a* of the base 3 is snugly fitted within the opening 6 formed in cap 5. As is well known, the outer end of stylus 4 is placed into contact with a patient's atlas or with some other vertebra that is to be realigned or adjusted.

For the purpose of imparting an impulse wave to the thrust pin 2, a percussion device 8 is reciprocably mounted within the housing 1 and is normally positioned within the housing 1 by releasable latch means comprising a latch pin 9 which is threaded into a threaded aperture 10 formed in percussion device 8. Latch pin 9 is arranged for insertion into one of the notches 11–14 formed along one edge of the longitudinal slot 15 formed in the housing 1. Movement of latch pin 9 generally upward as viewed in FIGS. 1 and 2 causes the latch pin to move out of one of the notches and thus rotates and releases the percussion device 8 and permits longitudinal movement of the percussion device 8 relative to housing 1.

For the purpose of imparting bodily movement to percussion device 8, energy storage means in the form of a compression spring 16 is disposed about the axial stem 8*a* of percussion device 8. The right hand end 16*a* of compression spring 16 is seated against the cap 17 having a threaded portion 18 for cooperating with the internal threads 19 formed at end 1*b* of housing 1. Obviously adjustment of the latch pin 9 in a direction longitudinally of the longitudinal slot 15 determines the force exerted by the spring 16 against the percussion device 8. Thus if latch pin 9 is disposed within notch 14 a maximum degree of compression of spring 16 is effected whereas lesser degrees of compression are effected when the latch pin 9 is disposed within any one of the notches 11, 12, or 13 as is obvious.

For the purpose of releasing the percussion device 8 for movement in the direction of thrust pin 2, a releasing trigger 20 is pivotally mounted at pivot 21 on handle means 22 which in turn is secured by pin 23 to housing 1. Pin 23 extends through aperture 24 formed in handle means 22 and is threadedly engaged with internally threaded aperture 25 formed in housing 1. This arrangement causes the trigger end 20*a* of releasing trigger 20 to occupy the elongated opening 25 formed in housing 1 and the longitudinally cutaway segment 8*b* formed in a side of percussion device 8. Obviously movement of releasing trigger 20 about its pivot imparts rotary motion to the percussion device 8 which is in a counterclockwise direction as viewed in FIG. 3 and such motion causes the latch pin 9 to move out of its associated notch 11, 12, 13 or 14 and frees the percussion device for sliding movement along the inside of housing 1 due to the force imparted by spring 16. This movement of percussion device 8 causes its axial stem 8*c* to impinge upon the center portion 3*b* of the base 3 of thrust pin 2. This impingement establishes an impulse wave which travels throughout the thrust pin 2 and particularly along the stylus 4 to impart an impulse to the patient's atlas or other vertebra. Such action is adequate for effecting realignment or adjustment of the atlas or vertebra and is of such character as not to cause injury to the patient because this impulse wave is not accompanied by any significant bodily movement of the thrust pin 2 in accordance with a principal feature of the invention.

Since this device is provided with the handle means 22 it is obviously well adapted for manual bodily movement to the desired angular relationship relative to the patient being treated. In order for the physician to determine accurately the angular disposition of the instrument, a conventional level mechanism generally designated by the numeral 26 is affixed to the cap 17 and is provided with angular indicating indicia 26a together with a bubble 26b. By means of the conventional level device 26, the physician may orient the instrument properly as may be desired for a particular circumstance. According to this invention, an appropriate practical device is provided in which the weight of the percussion device is approximately five ounces and the weight of the entire instrument exclusive of the weight of the percussion device is approximately one pound eleven ounces. A suitable maximum spring pressure when the spring is fully compressed has been found to exert a force of approximately four pounds.

INDUSTRIAL APPLICABILITY

As is obvious, an instrument formed according to this invention is adapted for use by physicians in chiropractic practice and is portable from place to place as may be desired. While the invention is particularly applicable to a manually handled instrument, the invention in its broader aspects is not limited to a portable device but is also applicable to a mechanism supported by a frame structure in a usable position relative to the body of the patient being treated.

I claim:

1. A chiropractic instrument comprising an elongated housing, an elongated thrust pin mounted within said housing and having one end projecting outwardly through one end of said housing, a percussion device reciprocably mounted within said housing and arranged with one part thereof normally spaced from the inner end of said thrust pin, releasable latch means arranged so as normally to secure said percussion device against reciprocable movement within said housing, and energy storage means arranged to impart bodily movement to said percussion device toward and into impingement with the inner end of said thrust pin in coordination with release of said latch means so as to establish an impulse wave along the length of said thrust pin the velocity of which is determined by the square root of the ratio of the Young's modulus to the density of the thrust pin material so that at the patient thrust pin interface and dependent on the impedance match, a portion of the energy imparted to the thrust pin is transmitted to the patient and a portion is reflected back to the percussion device and without imparting significant bodily movement to said thrust pin.

2. A chiropractice instrument according to claim 1 wherein said thrust pin is fixedly mounted within said housing.

3. A chiropractic instrument according to claim 1 wherein the weight of said percussion device is approximately five ounces.

4. A chiropractic instrument according to claim 1 wherein the weight of said instrument exclusive of the weight of said percussion device is approximately one pound eleven ounces.

5. A chriopractic instrument according to claim 1 wherein said energy storage means comprises a compression spring and wherein the maximum spring force exerted by said compression spring when fully compressed is approximately four pounds.

6. A chiropractic instrument comprising an elongated housing, an elongated thrust pin mounted within said housing and having one end projecting outwardly through one end of said housing, a percussion device reciprocably mounted within said housing and arranged with one part thereof normally spaced from the inner end of said thrust pin, releasable latch means arranged so as normally to secure said percussion device against reciprocable movement within said housing and including a longitudinal slot formed in a wall of said housing, at least one notch formed in one edge of said slot together with a latch pin secured to said percussion device and projecting radially outward therefrom and through said slot, said latch pin being normally disposed in said notch to latch said percussion device against movement relative to said housing and being movable out of said notch to release said percussion device for impingement with said thrust pin, energy storage means arranged to impart bodily movement to said percussion device toward and into impingement with the inner end of said thrust pin in coordination with release of said latch means so as to establish an impulse wave along the length of said thrust pin without imparting significant bodily movement thereto, a releasing trigger pivotally mounted on said housing and arranged with a part thereof projecting through an opening in said housing and into engagement with a part of said percussion device so that pivotal movement of said releasing trigger imparts bodily movement to said percussion device and to said latch pin whereby said latch pin disengages said notch.

7. A chiropractic instrument according to claim 6 wherein handle means is mounted on said housing and wherein said releasing trigger is pivotally mounted on said handle means.

8. A chiropractice instrument according to claim 6 wherein a longitudinal segment is formed in said percussion device for receiving said part of said releasing trigger whereby pivotal movement of said releasing trigger imparts rotary movement to said percussion device and releasing movement of said latch pin out of said notch.

9. A chiropractic instrument comprising an elongated housing, an elongated thrust pin mounted within said housing and having one end projecting outwardly through one end of said housing, a percussion device including a generally cylindrical body portion having a cutaway longitudinal segment and an axial stem projecting from each end and being reciprocably mounted within said housing and arranged with one part thereof normally spaced from the inner end of said thrust pin, releasable latch means arranged so as normally to secure said percussion device against reciprocable movement within said housing, and energy storage means arranged to impart bodily movement to said percussion device toward and into impingement with the inner end of said thrust pin in coordination with release of said latch means so as to establish an impulse wave along the length of said thrust pin without imparting significant bodily movement thereto.

* * * * *